(12) United States Patent  
Chiang

(10) Patent No.: US 8,248,092 B2  
(45) Date of Patent: Aug. 21, 2012

(54) CONDUCTIVITY MEASUREMENT DEVICE

(75) Inventor: Wen-Kai Chiang, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 320 days.

(21) Appl. No.: 12/563,173

(22) Filed: Sep. 21, 2009

(65) Prior Publication Data  
US 2010/0315104 A1 Dec. 16, 2010

(30) Foreign Application Priority Data  
Jun. 12, 2009 (CN) .......................... 2009 1 0303196

(51) Int. Cl.  
*G01R 31/20* (2006.01)  
*G01R 1/067* (2006.01)  
*G01R 31/00* (2006.01)

(52) U.S. Cl. ............ 324/754.1; 324/755.04; 324/755.05

(58) Field of Classification Search .................. None  
See application file for complete search history.

(56) References Cited

U.S. PATENT DOCUMENTS  
5,457,392 A * 10/1995 Filipescu ...................... 324/555  
2002/0171433 A1* 11/2002 Watanabe et al. ............. 324/539  
* cited by examiner

*Primary Examiner* — Roberto Velez  
(74) *Attorney, Agent, or Firm* — Altis Law Group, Inc.

(57) ABSTRACT

A conductivity measurement device comprises a first body, a second body, a baseplate, a extension rod and a contact pad. The extension rod is positioned inside the first body, the baseplate is positioned on one end of the extension rod, and the contact pad is positioned on the other end of the extension rod. The contact pad contacts the surface to be tested and measures the electrical conductivity thereof with no resulting damage to the surface.

8 Claims, 3 Drawing Sheets

CONDUCTIVITY MEASUREMENT DEVICE

BACKGROUND

1. Technical Field

The present application is related to a measurement device for electrical conduction.

2. Description of Related Art

Surfaces of some commonly produced electronic products are made of aluminum magnesium alloy, to achieve thin profile, light weight, and favorable appearance, while providing electromagnetic masking and heat dissipation functions. Conductive protection films are often applied on surfaces of those electronic products to isolate air and prevent aluminum magnesium alloy from oxidization decomposition. The protective film is very thin, and usually very easily scratched during procedures to measure the conductivity thereof. Therefore, a conductivity measurement device capable of effectively measuring conductivity of a thin protection film without damaging the surface is desired.

DETAILED DESCRIPTION

Figure 1:
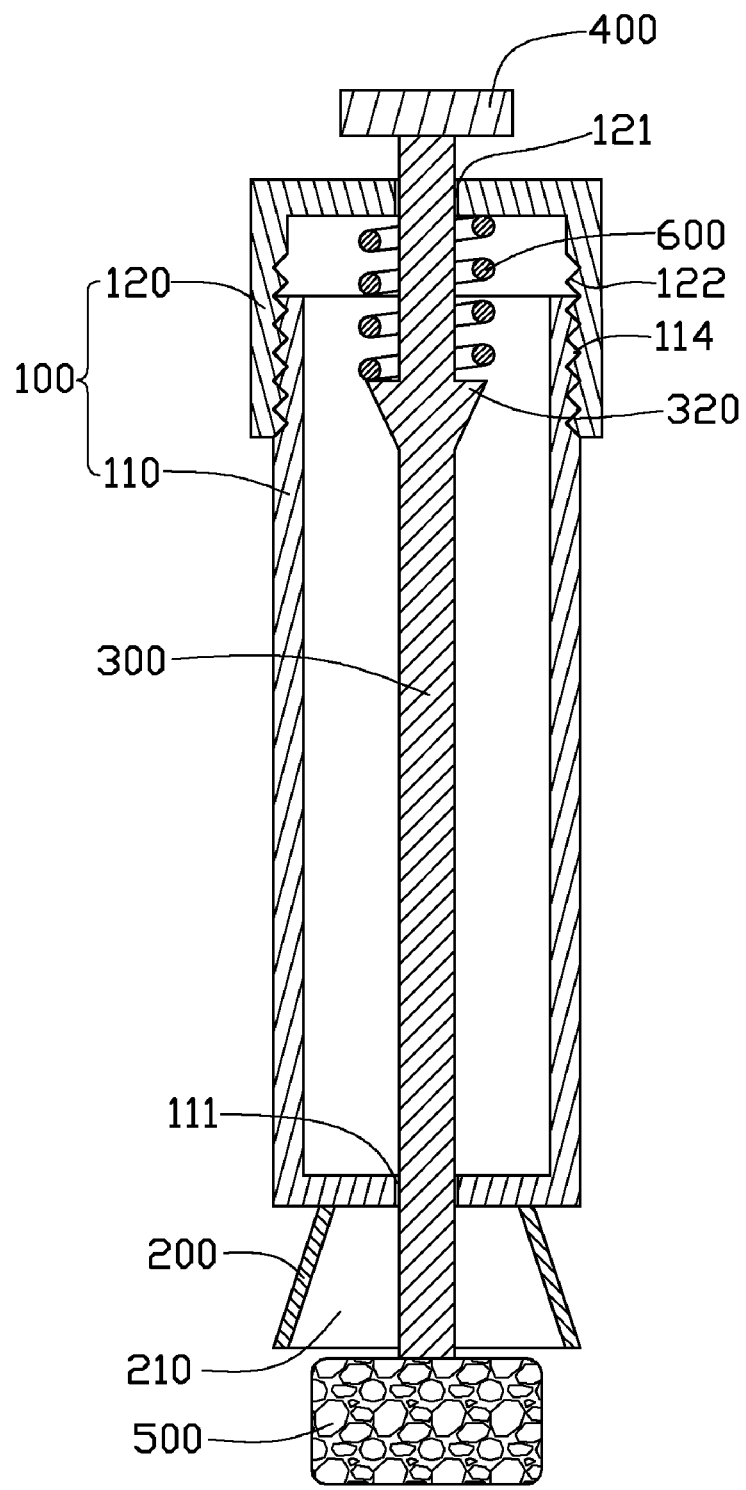
FIG. 1 is a cross-section of one embodiment of a conductivity measurement device of the present application.
Figure 2:
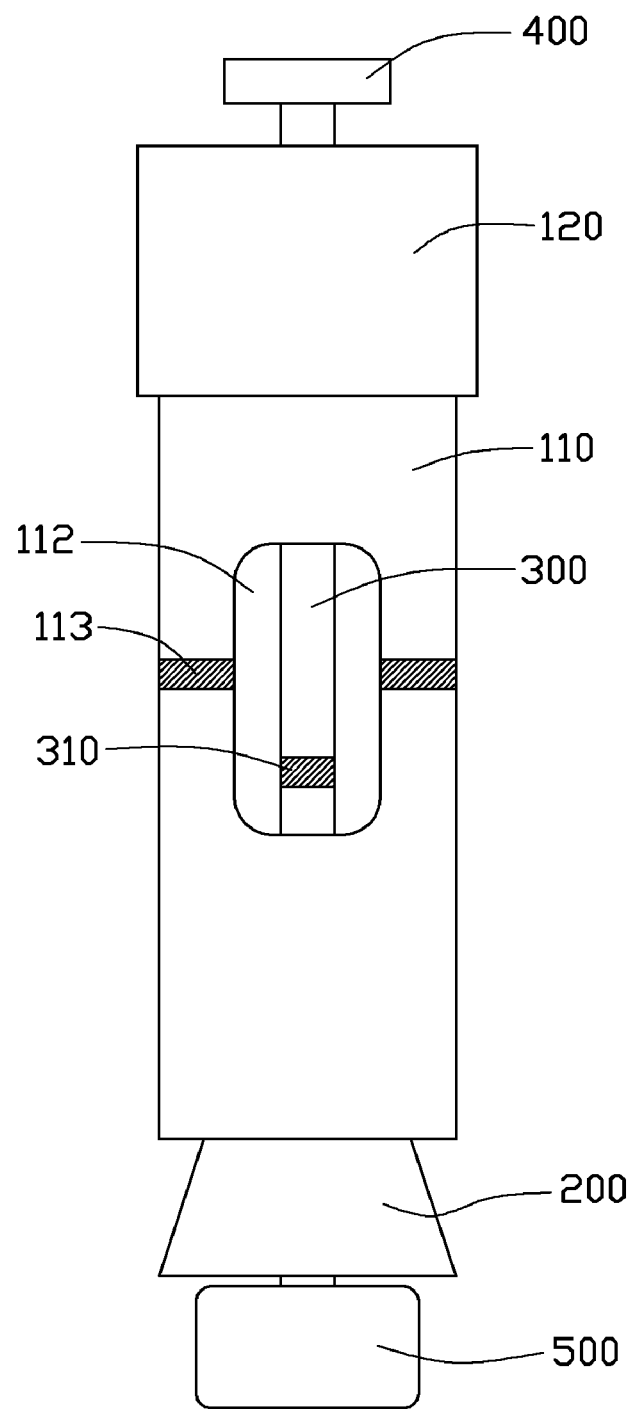
FIG. 2 is a schematic drawing showing the conductivity measurement device of the present application before measuring conductivity of a surface.

Referring to FIG. 1 and FIG. 2, the conductivity measurement device 10 of the present application comprises a first body 100, a second body 200 with a hollow structure, an extension rod 300, a baseplate 400, a contact pad 500, and a spring 600. The first body comprises a cylindrical barrel 110 with one open end, and a cap 120. An external thread 114 is provided outside the opening end of the barrel 110, and on the other end, a first through hole 111 is defined. A second through hole 121 is defined on one end of the cap 120, and an internal thread 122 is provided inside the other end of the cap 120, away from the second through hole 121. The barrel 110 and the cap 120 are connected by engagement of the internal thread 122 and the external thread 114. A transparent window 112 is positioned on the barrel 110, and a notice label 310, formed as a line marker, is on one side of the extension rod, facing the window 112. A center label 113, also formed as a line marker, is outside the barrel 110, extending from two vertical sides of the window 112 and parallel to the cap 120. In one embodiment of the present application, the first body 100 has a height of about 14 cm and a radius of about 0.7 cm.

The extension rod 300 is made of metal and shaped as a cylinder. The radius of the extension rod 300 is smaller than the radius of the first through hole 111 and the second through hole 121. A protruding fastening portion 320 is provided on the periphery of the extension rod 300, near the baseplate 400. The baseplate 400 is connected to a resistance meter (not shown) through a wire, and the contact pad 500 contacts a surface to be tested. In one embodiment of the present application, the contact pad 500 is a solid cylinder of electrically conductive sponge, with a radius of about 0.5 cm and a height of about 0.5 cm. In other embodiments, the contact pad 500 can be other material with similar electrical conductivity and pliability.

The spring 600 is configured to pass through the upper end of the extension rod 300, above the fastening portion 320, to facilitate retraction of the extension rod 300. One end of the extension rod 300, with the fastening portion 320 and the spring 600, is configured to pass through the second through hole 121 of the cap 120, and the other end of the extension rod 300 is configured to pass through the first through hole 111 of the barrel 110 and the second body 200 sequentially. The internal thread 122 and the external thread 114 are engaged to fasten the barrel 110 with the cap 120. The contact pad 500 is positioned to one end of the extension rod 300, proximal to the second body 200, and the baseplate 400 is positioned on the other end of the extension rod 300. The second body 200 is preferably shaped as a hollow frustum of a cone with one centimeter height, a first radius of about 0.5 centimeters and a second radius of about 0.7 centimeter.

Figure 3:
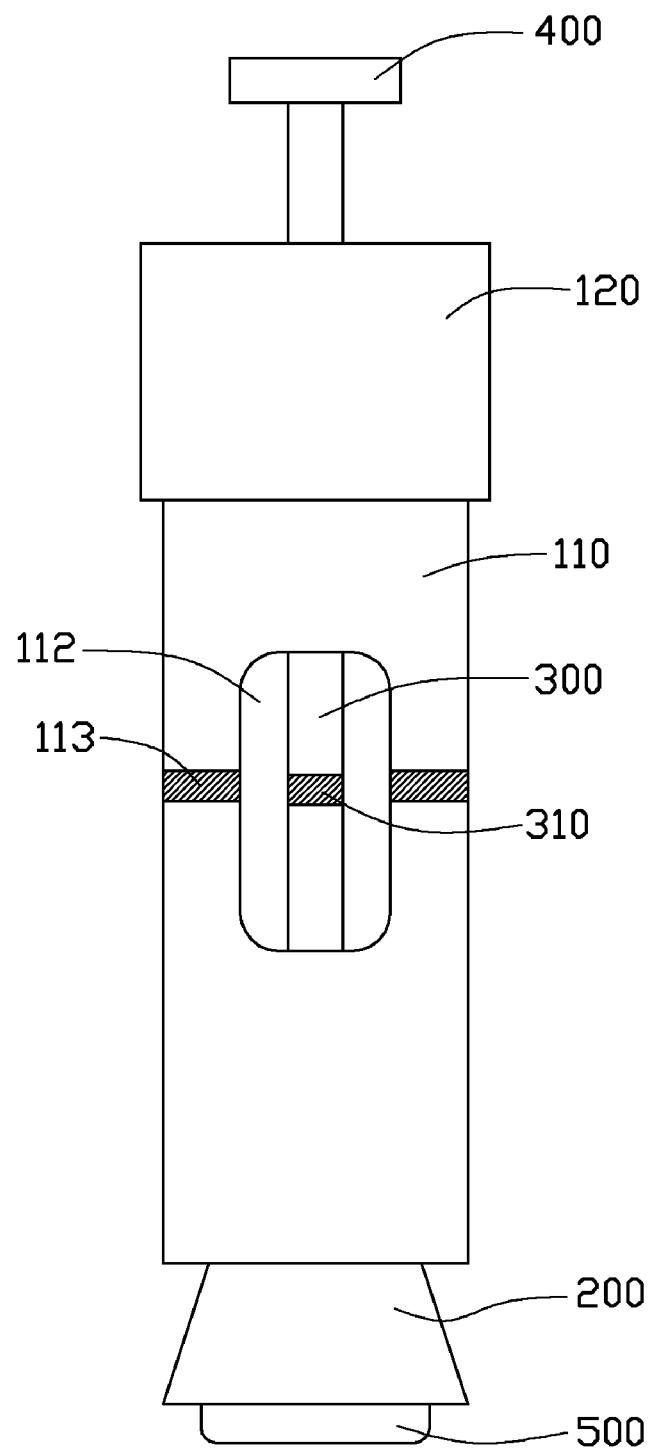
FIG. 3 is a schematic drawing showing the conductivity measurement device of the present application measuring conductivity of a surface.

Referring to FIG. 2, which shows a non-measuring status of the conductivity measurement device 10. Through the window 112, notice label 310 is configured not to align with the center label 113 for this status. Referring to FIG. 3, the conductivity measurement device 10 is shown in a measurement status, in which the barrel 110 is held and the contact pad 500 makes contact with the surface to be tested, with pressure applied toward the surface, such that the contact pad 500 is contracted into the second body 200, and the notice label 310 is moved to align with the center label 113. When the notice label 310 is fully aligned with the center label 113, the contact pad 500 has achieved full contact with the surface to be tested, and the conductivity of the surface to be tested is shown on the resistance meter. After finishing the measurement, pressure is released on the barrel 110, the spring 600 restores and the extension rod 300 returns to an original position, under the center label 113. The contact pad 500 is a soft detection body, thereby providing measurement of the conductivity of the surface to be tested with no damage to the surface.

While the present application has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A conductivity measurement device to measure a conductivity of a surface, the conductivity measurement device comprising:
   a first body,
   a baseplate;
   an extension rod; and
   a contact pad which is electrically conductive;
   wherein the extension rod is positioned inside the first body, the baseplate is positioned on one end of the extension rod, and the contact pad is mounted to the other end of the extension rod and contacts the surface; the contact pad is a soft detection body to avoid damaging the surface; and
   wherein a window is provided on an outer wall of the first body, a center label is provided aligned with the middle of the window, a notice label is provided on the extension rod, such that the notice label and the center label align when the conductivity of a surface to be tested is measured.

2. The conductivity measurement device as claimed in claim 1, further comprising a second body with a hollow structure and connected with the first body on one end, wherein the first body comprises a barrel and a cap, the cap is positioned on one end of the barrel, a first through hole is defined in another end of the barrel connected with the second body, a second through hole is defined in one end of the cap, one end of the extension rod protrudes from the second body via the first through hole, and the other end of the extension rod protrudes from the first body via the second through hole.

3. The conductivity measurement device as claimed in claim 2, wherein a fastening portion is positioned along the periphery of the end of extension rod, proximal to the second through hole, and a spring is positioned between the cap and the fastening portion.

4. The conductivity measurement device as claimed in claim 2, wherein the height of the barrel is 14 centimeters, and the radius of the barrel is 0.7 centimeters.

5. The conductivity measurement device as claimed in claim 2, wherein the second body shaped as a hollow frustum of a cone with one centimeter height, a first radius of 0.5 centimeters and a second radius of 0.7 centimeter.

6. The conductivity measurement device as claimed in claim 2, wherein an external thread is provided on the outer wall of the barrel, an internal thread is provided on the inner wall of a cap, and the barrel and the cap are engaged through the external thread and the internal thread.

7. The conductivity measurement device as claimed in claim 1, wherein the contact pad is a conductive sponge.

8. The conductivity measurement device as claimed in claim 7, wherein the radius of the soft sponge is 0.5 centimeters, and the height of the soft sponge is 0.5 centimeters.

* * * * *